United States Patent [19]

Habara

[11] Patent Number: 5,391,880
[45] Date of Patent: Feb. 21, 1995

[54] GAMMA CAMERA SYSTEM

[75] Inventor: Atsushi Habara, Otawara, Japan

[73] Assignee: Kabushiki Kaisha Toshiba, Kanagawa, Japan

[21] Appl. No.: 207,660

[22] Filed: Mar. 9, 1994

[30] Foreign Application Priority Data

Mar. 9, 1993 [JP] Japan ................... 5-048180

[51] Int. Cl.$^6$ .............................................. G01T 1/166
[52] U.S. Cl. ................................ 250/369; 250/363.04; 364/413.24
[58] Field of Search ................... 250/369, 363.04; 364/413.24

[56] References Cited

U.S. PATENT DOCUMENTS

| 4,223,388 | 9/1980 | Nishikawa et al. | 250/369 |
| 4,437,161 | 3/1984 | Anderson | 378/98.12 |
| 5,309,357 | 5/1994 | Stark et al. | 250/369 |

OTHER PUBLICATIONS

Matsui, S., "Dedicated SPECT Gamma Camera System with World's No. 1 Spatial Resolution," Toshiba Review, 1991, vol. 46, No. 2, pp. 101–104.

Primary Examiner—Carolyn E. Fields
Attorney, Agent, or Firm—Finnegan, Henderson, Farabow, Garrett & Dunner

[57] ABSTRACT

A gamma camera system is provided for obtaining a distribution image (i.e. a reconstruction and/or multiplanar reconstruction image) of a radioisotope injected into an object by dynamic study on the basis of $\gamma$-rays emitted from the radioisotope. The system comprises a two-dimensional detector for detecting the $\gamma$-rays, the detector being repeatedly rotated around the object. There are provided an element for forming image data of a reference image and the distribution image on the basis of detected signals from the detector, an element for obtaining a change in quantity of the $\gamma$-rays every one rotation of detector, an element for specifying one of the plurality of rotations, the specified rotation corresponding to a maximum number of the $\gamma$-rays, and an element for displaying the reference image using the reference image data corresponding to the specified one rotation. Further provided is an element for manually setting information required to obtain the distribution image using the displayed reference image. Using manually set information, the image data forming element creates the distribution image data.

16 Claims, 6 Drawing Sheets

GAMMA CAMERA SYSTEM

BACKGROUND OF THE INVENTION

The present invention relates to a gamma camera system used in medical examination, and in particular to the gamma camera system for single photon emission computed tomography (single photon ECT or SPECT), etc. performing dynamic study.

So far, diagnoses with a gamma camera system such as a SPECT apparatus have been known as one means for diagnosing the function of a patient's organ and/or tissue. Amongst such diagnoses, a dynamic study of imaging the change of such function in a specific slice over time has particularly become an indispensable means.

In this dynamic study, a detector is rotated about a diagnostic portion of a patient continuously N times (N is a positive integer: one rotation is referred to as "one repeat") and detects $\gamma$-ray radiated from a radioisotope (RI) injected into a patient, thereby acquiring a plurality of sets of repeat data for N-time rotation. One repeat data consists of one set of position data (i.e. projection data) obtained at every predetermined rotation angle during one time of rotation of the detector.

When a plurality of sets of repeat data has been obtained for N-time rotations, image reconstruction and/or multiplanar reconstruction (i.e., obtaining a cross-section image in an arbitrary direction from a three-dimensional image data that had been once acquired) are carried out based upon these data. In this time, a reference image is displayed on a monitor in the first place.

As a method for selecting this reference image, known is a method to designate, as a reference data, the position data for a predetermined fixed repeat (the second repeat or the third repeat, for example) and display this reference data. Also known is a method where an operator observes the images reconstructed and displayed for each repeat and searches the one considered to be the most optimal for the reference data.

When the reference image is displayed in these manners, an operator designates a scope of image reconstruction and/or a range and angle of multiplanar reconstruction with a cursor on the monitoring image. After this designation has been completed, the sets of all the repeat data are processed under the same conditions (scope, angle, etc.) as the ones designated for the reference image and are subjected to the image reconstruction and/or multiplanar reconstruction.

In the above-described prior art, however, there was a problem of inaccuracy and operation inefficiency in cursor setting necessary for image reconstruction and/or multiplanar reconstruction.

The reason is as follows. Generally, the data collection begins on the administration of RI in the dynamic study of SPECT. The RI accumulates on a target organ over a certain period of time and is excreted thereafter. For the accurate cursor setting required is the quality reference image.

Nevertheless, with the aforementioned conventional method (the first-described one), there is no guarantee that the reference image with the predetermined fixed repeat data is always of high quality. Especially, when the earlier repeat data such as the first repeat data is employed, the reference image is often reconstructed even before the RI accumulates on the target organ, thus being of low quality. Therefore, the cursor setting accuracy may be lowered and the designation as to the image reconstruction and/or multiplanar reconstruction could not be executed as desired.

To avoid this disadvantage, the operator may watch a monitor screen and search a reference image displayed thereon without predetermining a repeat as described above. This method, however, requires a great deal of labor and time, thus resulting in low operation efficiency. Further, since this method burdens the operator with much monitoring operation, it brings a problem that the diagnosis efficiency is forced to be lowered in total.

SUMMARY OF THE INVENTION

The present invention is made, taking into consideration the above-described drawbacks of the prior art. Accordingly, it is an object of the present invention to provide a gamma camera system capable of automatically displaying a quality reference image and enabling the cursor setting for image reconstruction and/or multiplanar reconstruction to be accurate and efficient.

To achieve the foregoing object, provided is a gamma camera system for obtaining a distribution image of a radioisotope injected into an object being examined by dynamic study on the basis of $\gamma$-ray emitted from the radioisotope, the system comprising: a detector for detecting the $\gamma$-rays; an element for repeatedly providing a plurality of relative rotations between the detector and the object; an element for forming image data including data of a reference image and data of the distribution image on the basis of detected signals from the detector; an element for obtaining a change in quantity of the $\gamma$-rays every one rotation among the plurality of relative rotations between the detector and the object; an element for specifying one of the plurality of relative rotations in conjunction with the change in the $\gamma$-ray quantity; and an element for displaying the reference image using the data of the reference image corresponding to the specified one rotation.

It is preferred that the gamma camera system is a single photon emission computed tomography system. Preferably, the detector has a two-dimensional incidence surface receiving the $\gamma$-rays. Also preferably, the relative rotation providing element is an element that provides rotations of the detector around the object being fixed. Further preferably, the obtaining element includes a counting-up element for counting up a number of the $\gamma$-rays for each of the relative rotations. It is preferred that the detector consists of a plurality of detectors for detecting the $\gamma$-rays and the counting-up element counts up the total number of the $\gamma$-rays reaching the plurality of detectors.

It is also preferred that the specifying element includes a reading element for reading a maximum $\gamma$-ray quantity in the change of the $\gamma$-rays and a determining element for determining the one of the plurality of relative rotations corresponding to the maximum $\gamma$-ray quantity. The system preferably comprises an element for manually setting information required to obtain the distribution image using the displayed reference image.

It is also preferred that the reference image is assigned to a projection image to be produced from the two-dimensional positions and the distribution image is assigned to a reconstruction image to be produced from the projection image. In this case, the manually setting element is able to set the information including a display range of the reconstruction image. Preferably, the image data forming element at least includes an element for calculating, every certain divided rotational angle of the detector in each of the plurality of rotations, two-dimensional positions of the γ-rays coming to the incidence surface of the detector, an element for acquiring data of the projection image made up of the two-dimensional positions, and an element for creating data of the reconstruction image in accordance with the data of the projection image and the information manually set. It is preferred to comprise an element for displaying the reconstruction image.

It is also preferred that the reference image is assigned to a reconstruction image to be produced from a projection image to be made from the two-dimensional positions and the distribution image is assigned to a multiplanar reconstruction image to be produced from the reconstruction image. In this case, the manually setting element is able to set the information concerning a display of the multiplanar reconstruction image. It is preferred that the image data forming element at least includes an element for calculating, every certain divided rotational angle of the detector in each of the plurality of rotations, two-dimensional positions of the γ-rays coming to the incidence surface of the detector, an element for acquiring data of a projection image made up of the two-dimensional positions, an element for first creating data of the reconstruction image using the data of the projection image, and an element for second creating data of the multiplanar reconstruction image in accordance with the data of the reconstruction image and the information manually set. Comprising an element for displaying the multiplanar reconstruction image is preferable.

BRIEF DESCRIPTION OF THE DRAWINGS

The accompanying drawings which are incorporated in and constitute a part of this specification, illustrate embodiments of the present invention and, together with the description, serve to explain the principles of the present invention. In the drawings.

DESCRIPTION OF THE PREFERRED EMBODIMENTS

A first embodiment of the present invention will be explained with reference to FIGS. 1 to 5 hereinafter.

Figure 1:
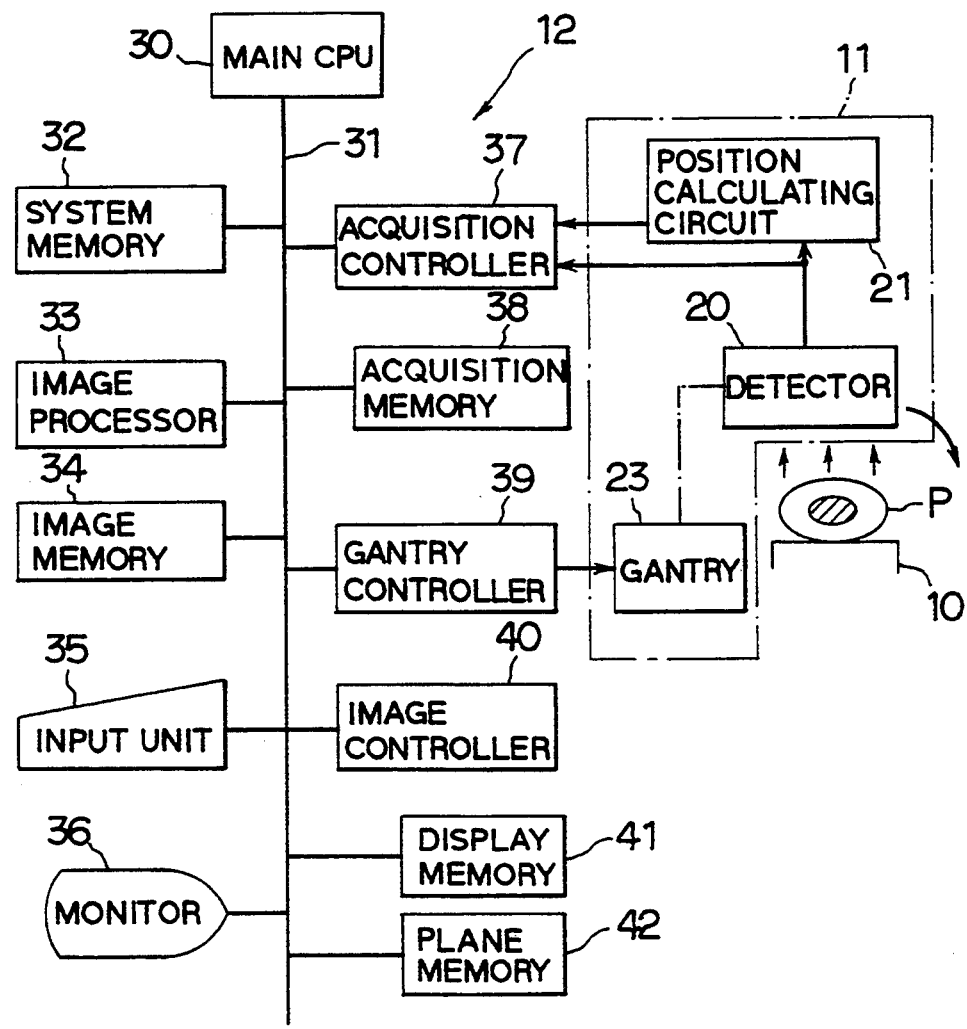
FIG. 1 is a block diagram illustrating a constitution of a SPECT system taken as a gamma camera system in accordance with a first embodiment of the present invention.

FIG. 1 illustrates with blocks the constitution of a SPECT system taken as a first embodiment of a gamma camera system in accordance with the present invention.

The SPECT system is provided with a gamma camera 11 rotatable about a diagnostic portion of a patient P lying on a couch 10 and an operator console 12 connected to the gamma camera 11.

The gamma camera 11 is furnished with a two-dimensional detector 20 having a collimator, scintillator, light guide, photomultiplier, etc. This detector 20 catches γ-rays emitted from an RI within the patient P and outputs electric pulse signals whose energy corresponds to the one of γ-ray lying within a designated range. These electric pulse signals are transmitted to a position calculating circuit 21 and the operator console 12. The position calculating circuit 21 calculates two-dimensional incidence positions of the γ-rays using the electric pulse signals and outputs to the operator console 12 electric position signals which correspond to so calculated positions. The detector 20 is supported rotatably by a gantry 23 which forms part of the gamma camera 11.

The operator console 12 is equipped with a main CPU (central processing unit) 30 controlling the whole system. This main CPU 30 has other processors and/or circuits connected to it via a bus system 31. That is, connected to the bus system 31 are a system memory 32, image processor 33, image memory 34, input unit 35 such as a keyboard, and monitor 36.

Also connected to the bus system 31 are an acquisition controller 37 and an acquisition memory 38 both constituting a data acquisition system. Inputted to the acquisition controller 37 are the foregoing electric pulse signal and position signal outputted, correspondingly to the γ-ray incidence, from the gamma camera 11. The acquisition memory 38 can store the collected data processed by the acquisition controller 37.

Further, connected to the bus system 31 is a gantry controller 39. This gantry controller 39 controls a rotation mechanism for the gantry 23 in the gamma camera 11 based on the instructions from the main CPU 30 and rotates the detector 20 about the diagnostic portion of the patient P.

Furthermore, connected to the bus system 31 are an image controller 40, display memory 41, and plane memory 42, all constituting an image processing system. In compliance with the instructions from the main CPU 30, the image controller 40 controls the image data's writing-in to the display memory 41 and its reading-out therefrom and a graphics data's reading-out from the plane memory 42. The display memory 41 is a memory that temporarily stores the acquisition data and graphic data so as to display images on the monitor 36. The plane memory 42 stores the graphic data which corresponds to graphic information including the position of a cursor that will be designated.

Concerning an image reconstruction, the processing carried out in the main CPU 30, acquisition controller 37, image controller 40 and image processor 33 will be explained with reference to FIG. 2. It is premised in this embodiment that a dynamic study starts on the administration of an RI into a patient P.

Figure 2:
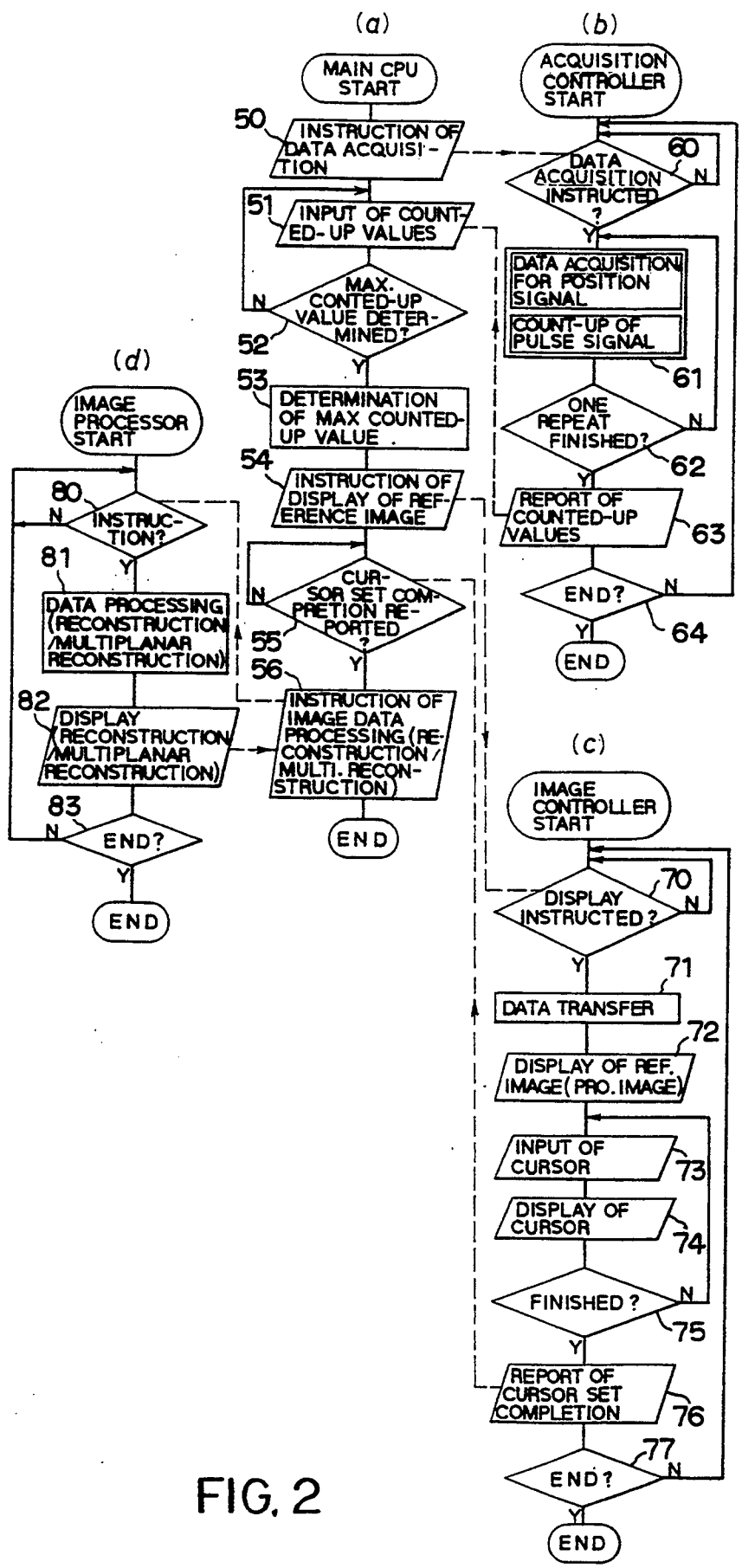
FIG. 2 is a flow chart illustrating the processings in a main CPU, an acquisition controller and an image controller in the first embodiment.

When the main CPU 30 receives the instructions of a dynamic study from an operator via the input unit 35, the main CPU 30 gives the gantry controller 39 the instructions to control the drive of the gantry 23 and runs in parallel a series of processings illustrated in FIG. 2-(a).

At first, the main CPU 30 instructs the acquisition controller 37 to collect data at step 50 shown in FIG. 2-(a).

Once the acquisition controller 37 receives the instructions, it judges YES at step 60 of the processing where it decides whether the acquisition controller 37 has been instructed to acquire data. Then, the processing goes to step 61 where, for every rotation of the detector 20, the acquisition controller 37 reads the position signal outputted from the gamma camera 11, forms the position data (i.e. projection data) of γ-rays radiated from the patient P and has such data stored in the acquisition memory 38, every rotation angle. In parallel with these processings, the acquisition controller 37 reads and counts up the pulse signals outputted from the detector 20, in correspondence with the γ-ray incidence, thereby determining an added-up value of such pulse signals obtained in one rotation of the detector, i.e. one repeat, for every repeat (steps 61 and 62 in FIG. 2-(b)). After this adding-up for every repeat is finished, transferring to step 63, the acquisition controller 37 reports all the counted-up values (added-up values) to the main CPU 30 (step 51 in FIG. 2-(a)). The processings above in the acquisition controller 37 are repeated until the whole processings are completed (step 64 in FIG. 2-(b)).

When the main CPU 30 receives the report of all the counted-up values at step 51 in FIG. 2-(a), it transfers to step 52 and judges whether it can determine a maximum among the counted-up values for every repeat reported. If a peak has been found out amongst a series of such counted-up values and the main CPU 30 judges that it could determine the maximum, it transfers to steps 53 and 54. However, if it has judged that it is early to determine the maximum, it returns to the step 51 and waits for the further report.

At the step 53, determined by the main CPU 30 is a repeat which has exhibited the maximum counted-up value.

At the step 54, designating such determined repeat, the main CPU 30 instructs the image controller 40 to display a reference image (step 70 in FIG. 2-(c)).

Figure 3:
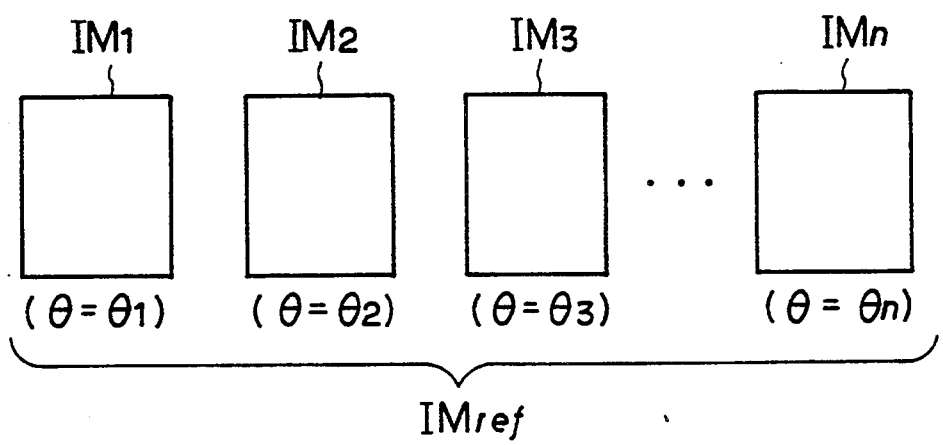
FIG. 3 is an illustration of a set of positional projection images.

When instructed to display a reference image, the image controller 40 judges YES at the step 70 in FIG. 2-(c). Then, the image controller 40 proceeds to step 71 and makes the position data at the repeat with the specified maximum counted-up value transferred from the acquisition memory 38 to the display memory 41. Next, at step 72, displayed on the monitor 36 in reduced multiple mode, for instance, are a series of projected image data (i.e. position data) stored frame by frame in the display memory 41. In this way, a reference image IMref based upon the positional projection data of γ-rays at the specified repeat is displayed on the monitor 36, as shown in FIG. 3. In FIG. 3, a reference numeral $\theta(=\theta1, \theta2, ...)$ represents a rotation angle of the detector 20 during a repeat, at which the positional projection data are each obtained.

Figure 4:
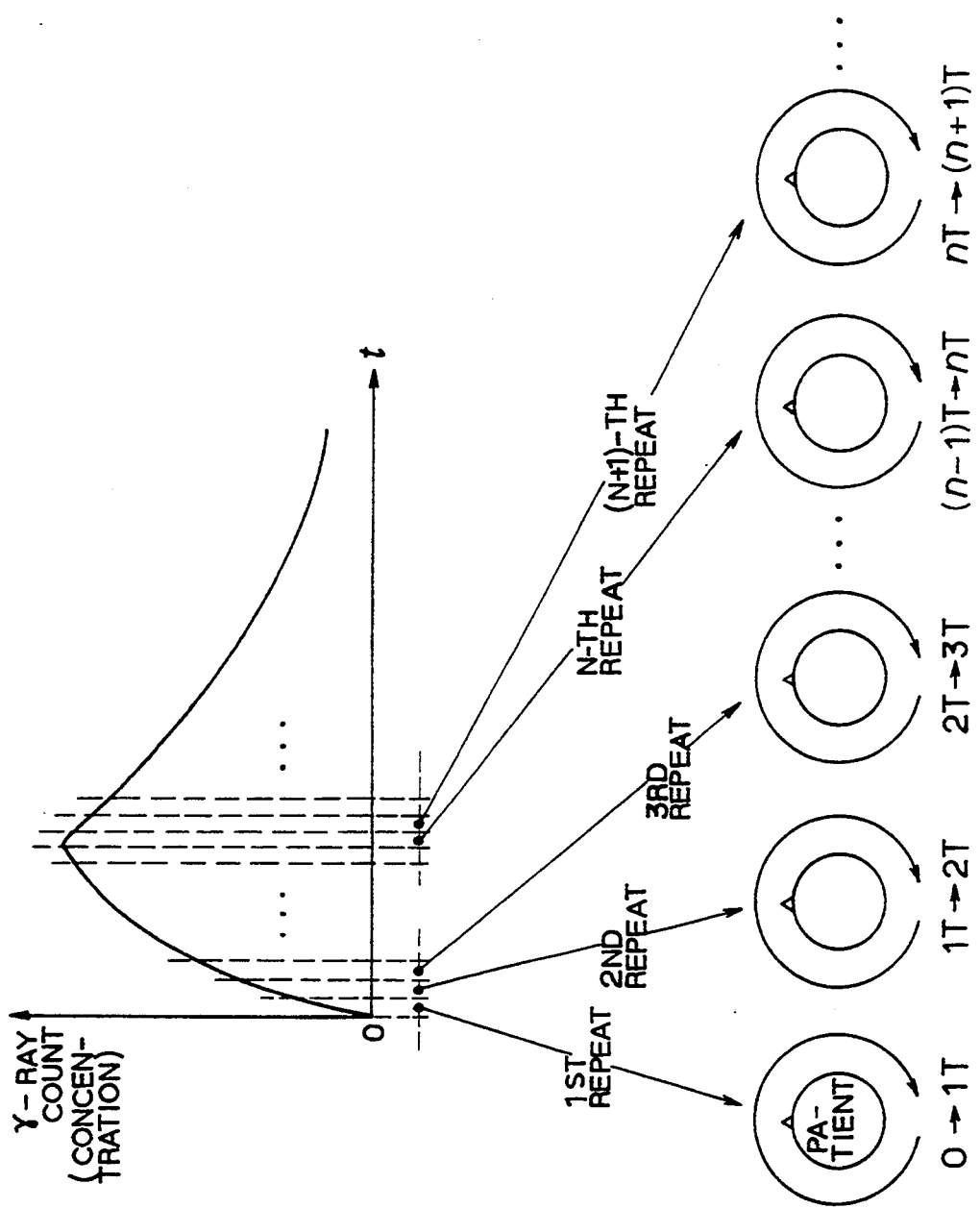
FIG. 4 is a schematic illustration explaining relationships between γ-ray count-up values and time duration of each repeat in a dynamic study executed in the SPECT system in FIG. 1.
Figure 5:
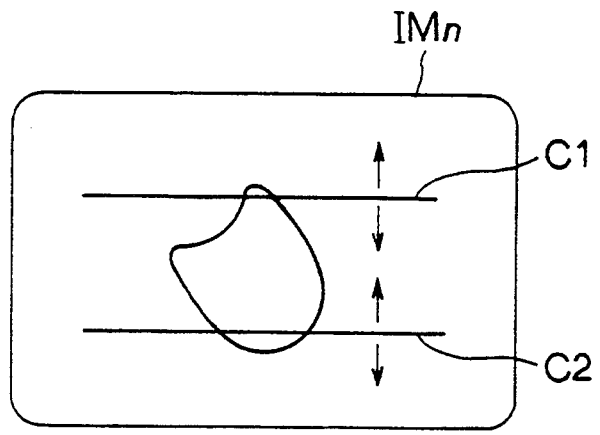
FIG. 5 is a schematic illustration showing the setting of a cursor in image reconstruction.

This reference image IMref, as shown therein, is made up of a plurality of positional projection images IM1, IM2, ..., IMn+1, ... produced during the n-th repeat (the time interval between (n−1)T and nT: T is a duration of one rotation of the detector) as shown in FIG. 4. Since the number of γ-ray pulses (i.e. counted-up value=image concentration) at this n-th repeat is the maximum on the count curve shown in FIG. 4, the image quality of such reference image IMref becomes the highest compared with images composed of positional projection data during other repeats.

Then, the processings of steps 73 to 75 are performed in turn. At the step 73, the operator inputs the information as of a desired position of a cursor, watching the reference image IMref on the monitor 36. This position information includes the one of cursors C1 and C2 related to image reconstruction as in FIG. 5. At the step 74, so set cursor is overlapped and displayed over the reference image IMref. At the step 75, it is judged whether the cursor setting is finished or not and, if YES, the processing goes to step 76.

At the step 76, it is reported to the main CPU 30 that the cursor setting has been finished (step 55 in FIG. 2-(a)). Even after this report of the cursor setting completion, the above-described processings are repeated if necessary (step 77 in FIG. 2-(c)).

When the main CPU 30 is notified that the cursor setting is completed, it judges YES at the step 55. Thus, it proceeds to step 56 and instructs the image processor 33 to carry out the processing of image reconstruction within the range set through the cursor. Following these instructions, the image reconstruction is carried out, under the same conditions as set for the reference image IMref on the monitor 36, in the image processor 33 through steps 80 to 83 shown in FIG. 2-(d).

In detail, when the image reconstruction is instructed at the step 80 (YES), the processing of the image reconstruction will be done according to a convolution back projection (CPB) method, for instance, at the next step 81. The processed data is then displayed on the monitor 36 at the next step 82.

According to the embodiment of dynamic study as explained above, the reference image of the highest quality is automatically displayed with the repeat data acquired at the time of an RI being sufficiently accumulated on a target organ. Consequently, the cursor setting for image reconstruction can be performed more accurately and within a shorter period of time. Namely, the operation efficiency for the cursor setting is remarkably improved as compared with the conventional system. Therefore, the present invention can contribute to the improvement of the throughput in the diagnosis as a whole. It also greatly lowers operator's burden to operate the system.

Figure 7:
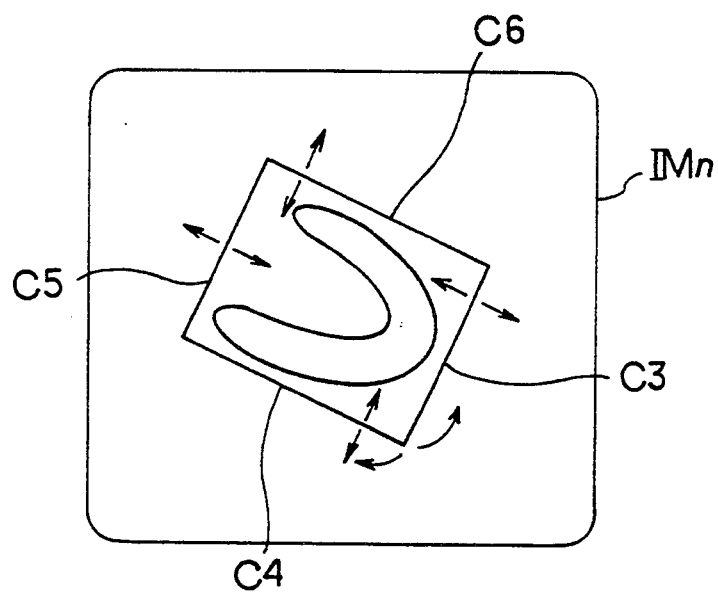
FIG. 7 is a schematic illustration showing the setting of a cursor in multiplanar reconstruction.

A second embodiment of the present invention will now be explained according to FIGS. 6 and 7.

The second embodiment concerns a SPECT system in which a multiplanar reconstruction can be additionally obtained as a distribution image (perfusion); in that case, the distribution image corresponds to a multiplanar reconstruction image and the reference image to a reconstruction image derived from the positional projection data. In this embodiment, a reconstruction image can also be obtained using a set of projection images as a reference image.

Figure 6:
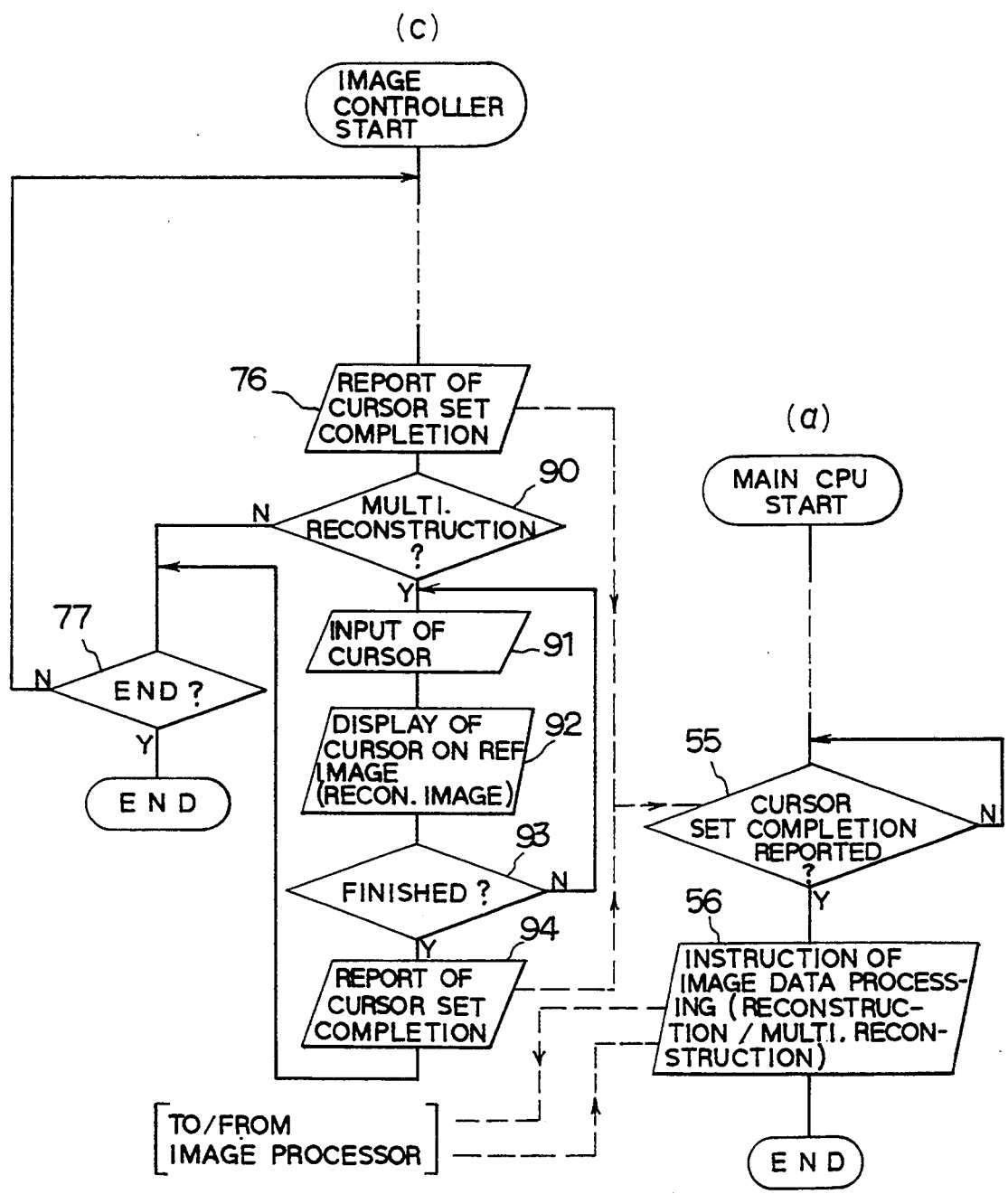
FIG. 6 is a flow chart illustrating the processings in a main CPU, an acquisition controller and an image controller in a second embodiment of the present invention.

In order to achieve the above multiplanar reconstruction, the processing shown in FIG. 6 is carried out in addition. In detail, after the step 76, a series of steps 90 to 94 will be followed by the image controller 40.

At the step 90, it is determined that a multiplanar reconstruction is carried out or not. If the determination is YES, inputted and displayed at the steps 91 and 92 is the position of a cursor for performing the multiplanar reconstruction, which is placed superimposedly on the reference image (i.e. a reconstruction image that has already been displayed in the same manner described in the first embodiment).

When this operation is finished, a report is sent to the main CPU 30 (refer to the steps 55 and 56), instructing the image processor 33 to start processing a multiplanar reconstruction image in compliance with the position (including an angle data) of the cursor that had been set. FIG. 7 shows one example of the cursor setting for a multiplanar reconstruction, in which line ROIs C3 to C6, forming the cursor, is used to specify a desired range and angle for the multiplanar reconstruction.

As a result, the processing of the multiplanar reconstruction is carried out within the range and at the angle set through the cursor. Therefore, even for obtaining a multiplanar reconstruction image, there are the similar advantages to the first embodiment.

Whereas the acquisition controller counts up the pulse signal generated corresponding to the γ-ray in the aforementioned embodiment, an independent counter may be provided to measure the pulse signal aside from this acquisition controller.

It is to be understood that the present invention is not limited to the SPECT system as described above. The present invention can be applied to other system, a positron emission computed tomography (PET), for example.

Further, although the above embodiments adopt one detector for detecting γ-rays, a plurality of such detectors may also be incorporated; in that case, the total number of γ-rays reaching all the detectors are counted up to recognize its maximum value.

Obviously, numerous modifications and variations of the present invention are possible in the light of the above teachings. It is therefore to be understood that within the scope of the appended claims, the invention may be practiced otherwise than as specifically described therein.

What we claim is:

1. A gamma camera system for obtaining a distribution image of a radioisotope injected into an object being examined by dynamic study on the basis of γ-rays emitted from the radioisotope, the system comprising:
    a detector for detecting the γ-rays;
    means for repeatedly providing a plurality of relative rotations between the detector and the object;
    means for forming image data including data of a reference image and data of the distribution image on the basis of detected signals from the detector;
    means for obtaining a change in quantity of the γ-rays every one rotation among the plurality of relative rotations between the detector and the object;
    means for specifying one of the plurality of relative rotations in conjunction with the change in the γ-ray quantity; and
    means for displaying the reference image using the data of the reference image corresponding to the specified one rotation.

2. A gamma camera system according to claim 1, wherein the gamma camera system is a single photon emission computed tomography system.

3. A gamma camera system according to claim 2, wherein the detector has a two-dimensional incidence surface receiving the γ-rays.

4. A gamma camera system according to claim 3, wherein the relative rotation providing means is a means that provides rotations of the detector around a fixed object position.

5. A gamma camera system according to claim 4, wherein the obtaining means includes a counting-up means for counting up a number of the γ-rays for each of the relative rotations.

6. A gamma camera system according to claim 5, comprising a plurality of detectors for detecting the γ-rays and the counting-up means is a means counting up the total number of the γ-rays reaching the plurality of detectors.

7. A gamma camera system according to claim 5, wherein the specifying means includes a reading means for reading a maximum γ-ray quantity in the change of the γ-rays and a determining means for determining the one of the plurality of relative rotations corresponding to the maximum γ-ray quantity.

8. A gamma camera system according to claim 7, the system further comprises means for manually setting information required to obtain the distribution image using the displayed reference image.

9. A gamma camera system according to claim 8, wherein the reference image is assigned to a projection image to be produced from the two-dimensional positions and the distribution image is assigned to a reconstruction image to be produced from the projection image.

10. A gamma camera system according to claim 9, wherein the manually setting means is a means that is able to set the information including a display range of the reconstruction image.

11. A gamma camera system according to claim 10, wherein the image data forming means at least includes means for calculating, every certain divided rotational angle of the detector in each of the plurality of rotations, two-dimensional positions of the γ-rays coming to the incidence surface of the detector, means for acquiring data of the projection image made up of the two-dimensional positions, and means for creating data of the reconstruction image in accordance with the data of the projection image and the information manually set.

12. A gamma camera system according to claim 11, the system further comprises means for displaying the reconstruction image.

13. A gamma camera system according to claim 8, wherein the reference image is assigned to a reconstruction image to be produced from a projection image to be made from the two-dimensional positions and the distribution image is assigned to a multiplanar reconstruction image to be produced from the reconstruction image.

14. A gamma camera system according to claim 13, wherein the manually setting means is a means that is able to set the information concerning a display of the multiplanar reconstruction image.

15. A gamma camera system according to claim 14, wherein the image data forming means at least includes means for calculating, every certain divided rotational angle of the detector in each of the plurality of rotations, two-dimensional positions of the γ-rays coming to the incidence surface of the detector, means for acquiring data of a projection image made up of the two-dimensional positions, means for first creating data of the reconstruction image using the data of the projection image, and means for second creating data of the multiplanar reconstruction image in accordance with the data of the reconstruction image and the information manually set.

16. A gamma camera system according to claim 15, the system further comprises means for displaying the multiplanar reconstruction image.

* * * * *